United States Patent
LesAulnier et al.

(10) Patent No.: US 6,503,479 B1
(45) Date of Patent: Jan. 7, 2003

(54) COSMETIC AEROSOL COMPOSITION FOR FIXING AND SHEEN OF KERATIN SUBSTANCES, AND PROCESSES

(75) Inventors: Claire-Marie LesAulnier, Paris; Jean-Michel Sturla, Boulogne Billancourt, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/802,939

(22) Filed: Feb. 21, 1997

(30) Foreign Application Priority Data

Feb. 22, 1996 (FR) .............................. 96 02206

(51) Int. Cl.$^7$ ................................. A61K 7/11
(52) U.S. Cl. .................. 424/45; 424/47; 424/DIG. 1; 424/DIG. 2; 424/70.11; 424/70.12; 514/63; 514/957
(58) Field of Search ................. 424/45, 47, DIG. 1, 424/DIG. 2, 70.11, 70.12; 514/957, 70.11, 63; 528/30

(56) References Cited

U.S. PATENT DOCUMENTS

| | | | |
|---|---|---|---|
| 4,724,851 A | * | 2/1988 | Cornwall et al. ........ 424/70.11 |
| 4,744,978 A | * | 5/1988 | Homan et al. ........... 424/70.11 |
| 4,749,565 A | * | 6/1988 | Grollier .................... 424/70.11 |
| 5,061,481 A | * | 10/1991 | Suzuki et al. |
| 5,120,812 A | * | 6/1992 | O'Lenick, Jr. et al. |
| 5,219,560 A | * | 6/1993 | Suzuki et al. |
| 5,294,437 A | * | 3/1994 | Shah et al. .............. 424/70.11 |
| 5,620,684 A | * | 4/1997 | Dupuis .................... 424/70.12 |
| 5,658,552 A | * | 8/1997 | Bünning et al. .............. 424/45 |
| 5,658,557 A | * | 8/1997 | Bolich, Jr. et al. |

FOREIGN PATENT DOCUMENTS

| | | | |
|---|---|---|---|
| AU | 18835 | * | 8/1993 |
| EP | 0205306 | | 12/1986 |
| FR | 2706296 | | 12/1994 |
| JP | 63-313713 | | 12/1968 |
| JP | 63-313714 | | 12/1968 |
| JP | 4-82820 | | 3/1992 |
| JP | 04-360812 | * | 12/1992 |
| WO | 28861 | * | 12/1994 |
| WO | 95/00108 | | 1/1995 |
| WO | 03776 | * | 2/1995 |

OTHER PUBLICATIONS

Gant, "Silicones for Ethnic Hair Care", Household and Personal Products Industry, vol. 20, No. 11, pp. 49–58, (1983).

Handt, "Hair Fixatives", Soap, Cosmetics, Chemical Specialties, vol. 63, No. 10, pp. 36–39 and 72–73.

* cited by examiner

*Primary Examiner*—Jose"G. Dees
(74) *Attorney, Agent, or Firm*—Finnegan, Henderson, Farabow, Garrett & Dunner

(57) ABSTRACT

The present invention relates to a cosmetic aerosol-pressurized composition for treating keratin substances, in particular the hair, comprising (a) a fluid comprising at least one fixing polymer and at least 5% by weight, relative to the total weight of the pressurized composition, of a non-volatile aryl silicone and (b) at least one propellant, as well as to a process for treating keratin substances using this composition.

43 Claims, No Drawings

COSMETIC AEROSOL COMPOSITION FOR FIXING AND SHEEN OF KERATIN SUBSTANCES, AND PROCESSES

The present invention relates to a cosmetic aerosol-pressurized composition for treating keratin substances, in particular the hair, comprising (a) a fluid comprising at least one fixing polymer and at least 5% by weight, relative to the total weight of the pressurized composition, of a non-volatile aryl silicone and (b) at least one propellant, as well as to a process for treating keratin substances using this composition.

In the cosmetics field, an aerosol-pressurized composition generally comprises a composition, known as the fluid, and a propellant agent.

Compositions for shaping or retaining the shape of the hair containing styling polymers (fixing polymers) in their formation generally have the drawback of making the disentangling, restyling or brushing of the hair difficult, in particular during blow-drying. Styling polymers also have a tendency to make the hair dull.

The combination of silicone derivatives with fixing polymers is known in cosmetic compositions for fixing and/or retaining the shape of the hairstyle. It has been observed that these silicone derivatives improve the disentangling, softness and sheen properties of hair treated with these compositions. However, on the one hand, silicone derivatives are not favorable to the styling properties of compositions containing fixing polymers, and, on the other hand, the sheen properties are still not satisfactory.

So-called "brilliant" products exist, which are applied as an end care product, that is to say on dried hair. These products are difficult to apply since if the amount applied is too large or poorly distributed, the head of hair generally has a greasy look and feel. Furthermore, these products provide no fixing.

Therefore,. the aim of the present invention is the preparation of compositions which allow the hairstyle to be fixed and/or shaped, these compositions having good hold properties over time and providing excellent sheen properties.

The present inventors have now discovered, surprisingly, that by using compositions containing a fixing polymer in combination with at least one non-volatile aryl silicone and at least one propellant in a cosmetically acceptable solvent, excellent sheen properties and a good drying time are obtained while at the same time having excellent styling and/or fixing properties.

The subject of the present invention is thus a cosmetic aerosol-pressurized composition comprising: (a) a fluid comprising, in a cosmetically acceptable medium, at least one fixing polymer and at least one non-volatile aryl silicone relative to the weight of the fluid; and (b) at least one propellant, wherein the concentration of the non-volatile aryl silicone is greater than or equal to 5% by weight relative to the total weight of the composition.

Surprisingly, despite the presence of a large amount of silicone, the decrease in fixing power of the compositions is limited. The styling properties are of the same degree as those of a composition containing only the fixing polymer. In particular, the fixing power, the hold over time and the volume of the head of hair are very good.

These compositions do not become powdery on the head of hair during brushing or combing (there are no white flakes) and are invisible on the hair. The treated hair has a non-greasy look and feel.

Furthermore, brushing and/or combing of the hair after application of the product further improves the sheen.

In the context of the present invention, the expression "cosmetic compositions for retaining the shape of the hairstyle" is understood to refer to any composition whose function is to fix the shape of the hairstyle temporarily, such as, for example, styling lacquers and sprays. The expression "fixing power of the composition" denotes that ability of the latter to give the hair a cohesion such that the initial shape of the hairstyle is conserved. The term "fixing polymer" is understood to refer to any polymer whose function is to fix the shape of the hairstyle temporarily.

According to the invention, any fixing polymer which is known per se can be used. In particular, fixing polymer selected from anionic, cationic, amphoteric and nonionic polymers and mixtures thereof can be used.

The fixing polymers may be used in solubilized form or in the form of dispersions of solid polymer particles.

The cationic fixing polymers which can be used according to the present invention are preferably selected from polymers containing primary, secondary, tertiary and/or quaternary amine groups forming part of the polymer chain or directly connected thereto, and having a molecular weight from 500 to about 5,000,000 and preferably from 1000 to 3,000,000.

Among these polymers, mention may preferably be made of the following cationic polymers:

(1) homopolymers or copolymers derived from acrylic or methacrylic esters or amides and containing at least one of the units of the following formulae:

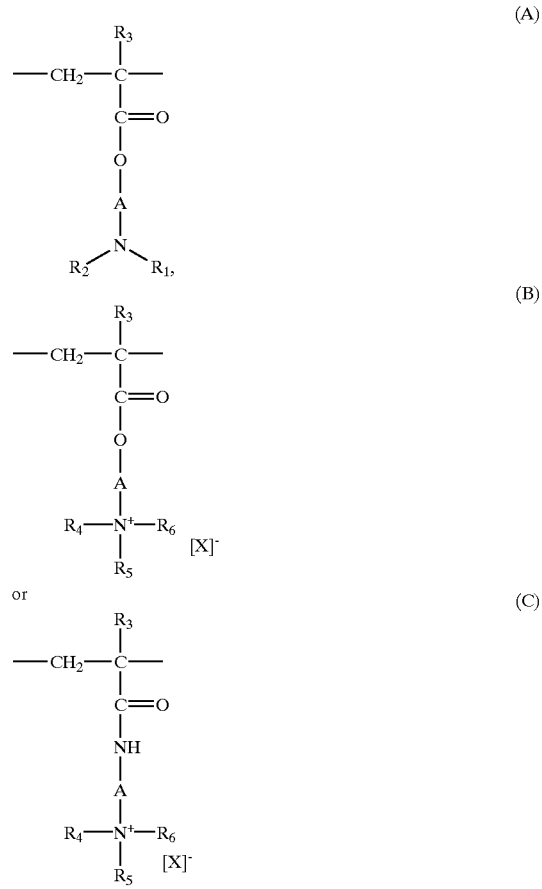

in which:

R$_3$ denotes a hydrogen atom or a CH$_3$ radical;

A is a linear or branched alkyl group of 1 to 6 carbon atoms or a hydroxyalkyl group of 1 to 4 carbon atoms;

R₄, R₅ and R₆, which are identical or different, represent an alkyl group having from 1 to 18 carbon atoms or a benzyl radical;

R₁ and R₂, which are indentical or different, represent hydrogen or an alkyl group having from 1 to 6 carbon atoms;

X denotes a methosulphate anion or a halide such as chloride or bromide; and (2) the quaternized polysaccharides described more particularly in U.S. Pat. Nos. 3,589,578 and 4,031,307, the disclosures of which are incorporated herein by reference, such as the product marketed under the name JAGUAR C 13S by the company Meyhall;

(3) quaternized copolymers of vinylpyrrolidone and of vinylimidazole;

(4) Chitosans or salts thereof, in particular, chitosan acetate, lactate, glutamate, gluconate or pyrrolidonecarboxylate.

Among these compounds, mention may be made of chitosan having a degree of deacetylation of 90.5%, sold under the name KYTAN BRUT STANDARD by the company Aber Technologies and chitosan pyrrolidonecarboxylate sold under the name KYTAMER PC by the company Amerchol.

The copolymers of group (1) also contain one or more monomer units which may be selected from acrylamides, methacrylamides, diacetone acrylamides, acrylamides and methacrylamides substituted on the nitrogen with $C_1$–$C_6$ lower alkyls, acrylic or methacrylic acids or esters thereof, vinyllactams, such as vinylpyrrolidone or vinylcaprolactam, and vinyl esters.

Thus, among these copolymers of group (1) mention may preferably be made of:

copolymers of acrylamide and of dimethylaminoethyl methacrylate quaternized with dimethyl sulphate or with a dimethyl halide, such as those sold under the name HERCOFLOC by the company Hercules;

copolymers of acrylamide and of methacryloyloxyethyltrimethylammonium chloride described, for example in European patent application EP-A-080,976, the disclosure of which is incorporated herein by reference, and sold under the name BINAQUAT P100 by the company Ciba Geigy;

the copolymer of acrylamide and of methacryloyloxyethyltrimethylammonium methosulphate sold under the name RETEN by the company Hercules;

quaternized or non-quaternized vinylpyrrolidone/ dialkylaminoalkyl acrylate or methacrylate copolymers, such as the products sold under the name GAFQUAT by the company ISP, such as, for example GAFQUAT 734 or GAFQUAT 755 or the products known as COPOLYMER 845, 958 and 937. These polymers are described in detail in French patents 2,077,143 and 2,393,573, the disclosures of which are incorporated herein by reference;

dimethylaminoethyl methacrylate/vinylcaprolactam/ vinylpyrrolidone terpolymers such as the product sold under the name GAFFIX VC 713 by the company ISP;

and the quaternized vinylpyrrolidone/ dimethylaminopropyl methacrylamide copolymer, such as the product sold Under the name GAFQUAT HS 100 by the company ISP;

The anionic fixing polymers generally used are polymers containing groups derived from carboxylic, sulphonic or phosphoric acid and have a weight-average molecular weight of approximately from 500 to 5,000,000.

The carboxylic groups are provided by unsaturated mono- or dicarboxylic acid monomers, such as those corresponding to the formula (II):

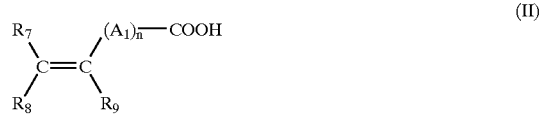

(II)

in which n is an integer from 0 to 10, $A_1$ denotes a methylene group, optionally linked to the carbon atom of the unsaturated group or to the neighbouring methylene group when n is greater than 1 via a hetero atom such as oxygen or sulphur, $R_7$ denotes a hydrogen atom, or a phenyl or benzyl group, $R_8$ denotes a hydrogen atom or a $C_1$–$C_6$ lower alkyl or carboxyl group and $R_9$ denotes a hydrogen atom, a $C_1$–$C_6$ lower alkyl group or a —$CH_2$—COOH, phenyl or benzyl group.

In the, abovementioned formula, a lower alkyl radical preferably denotes a group having 1 to 6 carbon atoms and in particular methyl and ethyl.

The preferred anionic fixing polymers containing carboxylic groups, according to the invention are:

(A) Homo- or copolymers of acrylic or methacrylic acid or salts thereof and in particular the products sold under the names VERSICOL E or K by the company Allied Colloid and ULTRAHOLD by the company BASF, and also the copolymers of acrylic acid and of acrylamide sold in the form of their sodium salt under the names RETEN 421, 423 or 425 by the company Hercules and the sodium salts of polyhydroxycarboxylic acids;

(B) Copolymers of acrylic or methacrylic acids with a monoethylenic monomer, such as ethylene, styrene, vinyl esters, esters of acrylic or methacrylic acid, optionally grafted onto a polyalkylene glycol, such as polyethylene glycol and optionally crosslinked. Such polymers are described in particular in French patent 1,222,944, the disclosure of which is incorporated herein by reference, and German patent application 2,330,956, the disclosure of which is incorporated herein by reference.

Copolymers of this type containing in their chain an optionally N-alkylated and/or hydroxyalkylated acrylamide unit as described, in particular, in Luxembourg patent applications 75370 and 75371, the disclosures of which are incorporated herein by reference, or as proposed under the name QUADRAMER by the company American Cyanamid. Mention may preferably be made of the copolymers of acrylic acid and of $C_1$–$C_4$ alkyl methacrylate and terpolymers of vinylpyrrolidone, of acrylic acid and of $C_1$–$C_{20}$ alkyl methacrylate, for example of lauryl methacrylate, such as that sold by the company ISP under the name ACRYLIDONE LM and methacrylic acid/ethyl acrylate/tert-butyl acrylate terpolymers such as the product sold under the name LUVIMER 100P by the company BASF;

(C) Copolymers derived from crotonic acid, such as those containing in their chain vinyl acetate or propionate units and optionally other monomers such as allylic or methallylic esters, vinyl ether or vinyl ester of a linear or branched saturated carboxylic acid with a long hydrocarbon chain, such as those containing at least 5 carbon atoms, it being possible for these polymers optionally to be grafted and crosslinked; or alternatively a vinyl, allylic or methallylic ester of an α- or β-cyclic carboxylic acid for example those described, inter alia, in French patents 1,222,944, 1,580,545, 2,265,782, 2,265,781, 1,564,110 and 2,439,798, the disclosures of which are incorporated herein by reference. Commercial products entering into this class are the resins 28-29-30, 26-13-14 and 28-13-10 sold by the company National Starch;

(D) Copolymers derived from $C_4$–$C_8$ monounsaturated carboxylic acids or anhydrides selected from:

copolymers comprising (i) one or more maleic, fumaric or itaconic acids or anhydrides and (ii) at least one monomer selected from vinyl esters, vinyl ethers, vinyl halides, phenylvinyl derivatives, and acrylic acid and esters thereof, the anhydride functions of these copolymers optionally being monoesterified or monoamidated, such polymers are described in particular in U.S. Pat. Nos. 2,047,398, 2,723,248 and 2,102,113 and GB patent 839,805, the disclosures of which are incorporated herein by reference and in particular those sold under the names GANTREX AN or ES by the company ISP;

copolymers comprising (i) one or more maleic, citraconic or itaconic anhydrides and (ii) one or more monomers selected from allylic or methallylic esters optionally containing one or more acrylamide, methacrylamide or α-olefin group, acrylic or methacrylic esters, acrylic or methacrylic acids or vinylpyrrolidone in their chain, the anhydride functions of these copolymers optionally being monoesterified or monoamidated, as described, for example, in French patents 2,350,384 and 2,357,241 the disclosures of which are incorporated herein by reference; and E) polyacrylamides containing carboxylate groups.

The polymers comprising sulphonic groups are polymers containing vinylsutphonic, styrenesulphonic, naphthalene-sulphonic or acrylamidoalkylsulphonic units.

These polymers may be selected in. particular from:

polyvinylsulphonic acid salts. having a weight-average molecular weight of approximately from 1000 to 100,000, as well as copolymers with an unsaturated monomer, such as acrylic or methacrylic acids and esters thereof, as well as acrylamide or derivatives thereof, vinyl ethers and vinylpyrrolidone;

polystyrenesulphonic acid salts, the sodium salts having a weight-average molecular weight of about 500,000 and of about 100,000 sold respectively under the names FLEXAN 500 and FLEXAN 130 by National Starch as described in French patent FR 2,198,719 the disclosure of which is incorporated herein by reference; and polyacrylamidesulphonic acid salts, such as those mentioned in U.S. Pat. No. 4,128,631, the disclosure of which is incorporated herein by reference, and, more preferably, polyacrylamidoethylpropanesulphonic acid sold under the name COSMEDIA POLYMER HSP 1180 by Henkel.

According to the invention, the anionic fixing polymers are preferably selected from acrylic acid copolymers such as the acrylic acid/ethyl acrylate/N-tert-butylacrylamide terpolymer sold under the name ULTRAHOLD STRONG by the company BASF, copolymers derived from crotonic acid, such as vinyl acetate/vinyl tert-butylbenzoate/crotonic acid terpolymers and crotonic acid/vinyl acetate/vinyl neodo-decanoate terpolymers sold under the name RESIN 28-29-30 by the company National Starch, polymers derived from maleic, fumaric or itaconic acids or anhydrides with vinyl esters, vinyl ethers, vinyl halides, phenylvinyl derivatives, acrylic acid and esters thereof, such as the monoesterified methyl vinyl ether/maleic anhydride copolymer sold under the name GANTREZ ES 425 by the company ISP, copolymers of methacrylic acid and of methyl methacrylate sold under the name EUDRAGIT L by the company Rohm Pharma, the copolymer of methacrylic acid and of ethyl acrylate sold under the name LUVIMER MAEX or MAE by the company BASF and the vinyl acetate/crotonic acid copolymer sold under the name LUVISET CA 66 by the company BASF and the vinyl acetate/crotonic acid copolymer grafted with polyethylene glycol, sold under the name ARISTOFLEX A by the company BASF.

The anionic fixing polymers most particularly preferred are selected from the monoesterified methyl vinyl ether/maleic anhydride copolymer sold under the name GANTREX ES 425 by the company ISP, the acrylic acid/ethyl acrylate/N-tert-butylacrylamide terpolymer sold under the name ULTRAHOLD Strong by the company BASF, the copolymers of methacrylic acid and of methyl methacrylate sold under the name EUDRAGIT L by the company Rohm Pharma, the vinyl acetate/vinyl tert-butylbenzoate/crotonic acid terpolymers and the crotonic acid/vinyl acetate/vinyl neododecanoate terpolymers sold under the name RESIN 28-29-30 by the company National Starch, the copolymer of methacrylic acid and of ethyl acrylate sold under the name LUVIMER MAEX or MAE by the company BASF and the terpolymer of vinylpyrrolidone/acrylic acid/lauryl methacrylate sold under the name ACRYLIDONE LM by the company ISP.

The amphoteric fixing polymers which can be used in accordance with the invention may be selected from polymers containing units B and C randomly distributed in the polymer chain, where B denotes a unit derived from a monomer containing at least one basic nitrogen atom and C denotes a unit derived from an acidic monomer containing one or more carboxylic or sulphonic groups, or alternatively B and C can denote groups derived from zwitterionic monomers of carboxybetaines or of sulphobetaines; B and C can also denote a cationic polymer chain containing primary, secondary, tertiary or quaternary amine groups in which at least one of the amine groups bears a carboxylic or sulphonic group connected via a hydrocarbon radical, or alternatively B and C form part of a chain of a polymer containing an α, β-dicarboxylic ethylene unit in which one of the carboxylic groups has been made to react with a polyamine containing one or more primary or secondary amine groups.

The amphoteric fixing polymers more particularly preferred corresponding to the definition given above are selected from the following polymers:

(1) Polymers resulting from the copolymerization of a monomer derived from a vinyl compound bearing a carboxylic group such as, more particularly, acrylic acid, methacrylic acid, maleic acid or α-chloroacrylic acid and of a basic monomer derived from a substituted vinyl compound containing at least one basic atom such as, more particularly, dialkylaminoalkyl methacrylate and acrylate, dialkylaminoalkylmethacrylamide and acrylamide. Such compounds are described in U.S. Pat. No. 3,836,537, the disclosure of which is incorporated herein by reference.

(2) Polymers containing units derived from:
  (a) at least one monomer selected from acrylamides or methacrylamides substituted on the nitrogen with an alkyl radical,
  (b) at least one acidic comonomer containing one or more reactive carboxylic groups, and
  (c) at least one basic comonomer, such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide and N-dodecylacrylamide as well as the corresponding methacrylamides.

The acidic comonomers are preferably selected from acrylic, methacrylic, crotonic, itaconic, maleic and fumaric acids as well as the alkyl monoesters having 1 to 4 carbon atoms of maleic or fumaric acids or anhydrides.

The preferred basic comonomers are aminoethyl, butylaminoethyl, N-N'-dimethylaminoethyl or N-tert-butylaminoethyl methacrylates.

Copolymers whose CTFA (4th Ed., 1991) name is octylacrylamide/acrylates/butylaminoethyl methacrylate copolymer, such as the products sold under the name AMPHOMER or LOVOCRYL 47 by the company National Starch, are preferably used.

(3) Partially or totally crosslinked and alkylated polyaminoamides derived from polyaminoamides of formula (III):

(III)

in which $R_{10}$ represents a divalent radical derived from a saturated dicarboxylic acid, from a mono- or dicarboxylic aliphatic acid containing a ethylenic double bond, from an ester of a lower alkanol having 1 to 6 carbon atoms of these acids or from a radical derived from the addition of any one of the said acids to a bis-primary or bis-secondary amine, and Z denotes a radical of a bis-primary, mono- or bis-secondary polyalkylene-polyamine and preferably represents:

(a) in proportions of from 60 to 100 mol % the radical (IV)

(IV)

where x=2 and p=2 or 3, or alternatively x=3 and p=2 the radical (IV) being derived from diethylenetriamine, from triethylenetetraamine or from dipropylenetriamine;

(b) in proportions of from 0 to 40 mol %, the radical (IV) above in which x=2 and p=1 and which is derived from ethylenediamine, or the radical derived from piperazine:

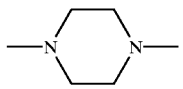

(c) in proportions of from 0 to 20 mol %, the —NH—(CH$_2$)$_6$—NH— radical being derived from hexamethylenediamine, these polyaminoamines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyaminoamide and alkylated by the action of acrylic acid, chloroacetic acid or an alkane sultone or salts thereof.

The saturated carboxylic acids are preferably selected from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic, methacrylic and itaconic acids.

The alkane sultones used in the alkylation are preferably propane or butane sultone, and the salts of the alkylating agents are preferably the sodium or potassium salts.

(4) Polymers containing zwitterionic units of formula (V):

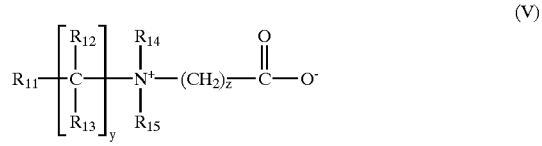

(V)

in which $R_{11}$ denotes a polymerizable unsaturated group such as an acrylate, methacrylate, acrylamide or methacrylamide group, y and z represent an integer from 1 to 3, $R_{12}$ and $R_{13}$, which are identical or different, represent a hydrogen atom, methyl, ethyl or propyl and $R_{14}$ and $R_{15}$, which are identical or different, represent a hydrogen atom or an alkyl radical such that the sum of the carbon atoms in $R_{14}$ and $R_{15}$ does not exceed 10.

The polymers comprising such units can also contain units derived from non-zwitterionic monomers, such as dimethyl or diethylaminoethyl acrylate or methacrylate or alkyl acrylates, acrylamides or methacrylamides or vinyl acetate.

By way of example, mention may preferably be made of the copolymer of methyl methacrylate/methyl dimethylcarboxymethylammonioethyl-methacrylate, such as the product sold under the name DIAFORMER Z301 by the company Sandoz.

(5) Chitosan-derived polymers containing monomer units corresponding to the following formulae:

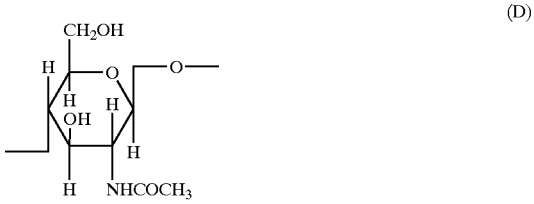

(D)

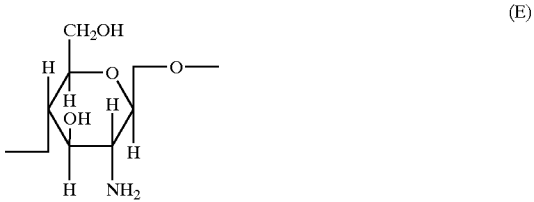

(E)

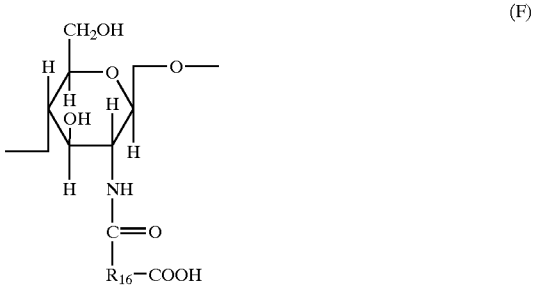

(F)

the unit D being present in proportions from 0 to 30%, the unit E in proportions from 5 to 50% and the unit F in proportions from 30 to 90%, it being understood that in this unit F, $R_{16}$ represents a radical of formula:

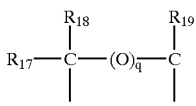

in which, if q=0, $R_{17}$, $R_{18}$ and $R_{19}$, which are identical or different, each represent a hydrogen atom, a methyl, hydroxyl, acetoxy or amino residue, a monoalkylamino residue or a dialkylamino residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being in this case a hydrogen atom;

or if q=1, $R_{17}$, $R_{18}$ and $R_{19}$ each represent a hydrogen atom, as well as the salts formed by these compounds with acids or bases.

(6) Polymers derived from the N-carboxyalkylation of chitosan, such as N-carboxymethyl chitosan or N-carboxybutyl chitosan sold under the name "EVALSAN" by the company Jan Dekker.

(7) Polymers corresponding to the general formula (VI) are described, for example, in French patent 1,400,366, the disclosure of which is incorporated herein by reference:

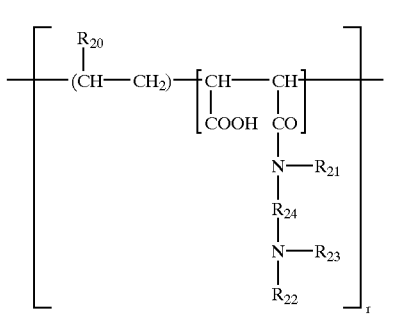

(VI)

in which $R_{20}$ represents a hydrogen atom or a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical, such as methyl or ethyl, $R_{23}$ denotes a lower alkyl radical such as methyl or ethyl or a radical corresponding to the formula: $-R_{24}-N(R_{22})_2$, $R_{24}$ representing a $-CH_2-CH_2-$, $-CH_2-CH_2-CH_2-$ or $-CH_2-CH(CH_3)-$ group, $R_{22}$ having the meanings mentioned above, as well as the higher homologues of these radicals containing up to 6 carbon atoms.

(8) Amphoteric polymers of the type —D—X—D—X selected from:

(a) polymers obtained by the action of chloroacetic acid or sodium chloroacetate on compounds containing at least one unit of formula (VII)

—D—X—D—X—D— (VII)

where D denotes a radical

and X denotes the symbol E or E', E or E', which are identical or different, denote a divalent radical which is an alkylene radical with a straight or branched chain containing up to 7 carbon atoms in the main chain, which is unsubstituted or substituted with hydroxyl groups and which can also contain oxygen, nitrogen or sulphur atoms and 1 to 3 aromatic and/or heterocyclic rings; the oxygen, nitrogen and sulphur atoms being present in the form of ether, thioether, sulphoxide, sulphone, sulphonium, alkylamine and alkenylamine groups, hydroxyl, benzylamine, amine oxide, quaternary ammonium, amide, imide, alcohol, ester and/or urethane groups; and (b) polymers of formula (VII'):

—D—X—D—X— (VII')

where D denotes a radical

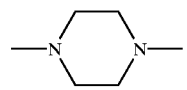

and X denotes the symbol E or E' with E' occurring at least once; E having the meaning indicated above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain optionally interrupted with an oxygen atom and necessarily containing one or more carboxyl functions or one or more hydroxyl functions and betainized by reaction with chloroacetic acid or sodium chloroacetate.

(9) Copolymers of $(C_1-C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl comonomers such as vinylcaprolactam.

The amphoteric fixing polymers particularly preferred according to the invention are those of group (3), such as the copolymers whose CTFA name is octylacrylamide/acrylates/butylaminoethyl methacrylate copolymer such as the products sold under the names AMPHOMER, AMPHOMER LV 71 or LOVOCRYL 47 by the company National Starch and those of group (4) such as the copolymer of methyl methacrylate/methyl dimethylcarboxymethylammonioethylmethacrylate sold, for example, under the name DIAFORMER Z301 by the company Sandoz.

The nonionic fixing polymers which can be used according to the present invention are selected, for example, from:

polyalkyloxazolines such as the polyethyloxazolines marketed by the company Dow Chemical under the names PEOX 50 000, PEOX 200 000 and PEOX 500 000;

vinyl acetate homopolymers such as the product marketed under the name APPRETAN EM by the company Hoechst or the product marketed under the name RHODOPAS A 012 by the company Rhône-Poulenc;

copolymers of vinyl acetate and of acrylic ester, such as the product marketed under the name RHODOPAS AD 310 by Rhône-Poulenc;

copolymers of vinyl acetate and of ethylene, such as the product marketed under the name APPRETAN TV by the company Hoechst;

copolymers of vinyl acetate and of maleic ester, for example of dibutyl maleate, such as the product marketed under the name APPRETAN MB Extra by the company Hoechst;

vinyl chloride homopolymers such as the products marketed under the names GEON 460X45, GEON 460X46 and GEON 577 by the company Goodrich;

polyethylene waxes such as the products marketed under the names AQUACER 513 and AQUACER 533 by the company Byk Cera;

polyethylene/polytetrafluoroethylene waxes such as the products marketed under the names DREWAX D-3750 by the company Drew Ameroid and WAX DISPERSION WD-1077 by the company R.T. Newey;

copolymers of polyethylene and of maleic anhydride;

alkyl acrylate homopolymers and alkyl methacrylate homopolymers, such as the product marketed under the name MICROPEARL RQ 750 by the company Matsumoto or the product marketed under the name LUHYDRAN A 848 S by the company BASF;

copolymers of acrylic esters such as, for example, the copolymers of alkyl acrylates and of alkyl methacrylates, such as the products marketed by the company Rohm & Haas under the names PRIMAL AC-261 K and EUDRAGIT NE 30 D, by the company BASF under the names ACRONAL 601, LUHYDRAN LR 8833 or 8845, and by the company Hoechst under the names APPRETAN N 9213 or N 9212;

copolymers of acrylonitrile and of a nonionic monomer selected, for example, from butadiene and alkyl (meth)acrylates; mention may preferably be made of the products marketed under the names NIPOL LX 531 B by the company Nippon Zeon or those marketed under the name CJ 0601 B by the company Rohm & Haas;

styrene homopolymers such as the product RHODOPAS 5051 marketed by the company Rhône-Poulenc;

copolymers of styrene and of alkyl (meth)acrylate such as the products MOWILITH LDM 6911, MOWILITH DM 611 and MOWILITH LDM 6070 marketed by the company Hoechst and the products RHODOPAS SD 215 and RHODOPAS DS 910 marketed by the company Rhône-Poulenc;

copolymers of styrene, of alkyl methacrylate and of alkyl acrylate, such as the product DAITISOL SPA marketed by the company Wacker;

copolymers of styrene and of butadiene such as the products RHODOPAS SB 153 and RHODOPAS SB 012 marketed by the company Rhône-Poulenc;

copolymers of styrene, of butadiene and of vinylpyridine, such as the products GOODRITE SB VINYLPYRIDINE 2528X10 and GOODRITE SB VINYLPYRIDINE 2508 marketed by the company Goodrich;

polyurethanes, such as the products marketed under the names ACRYSOL RM 1020 or ACRYSOL RM 2020 by the company Rohm & Haas and the products URAFLEX XP 401 UZ and URAFLEX XP 402 UZ by the company DSM Resins;

copolymers of alkyl acrylate and of urethane such as the product 8538-33 by the company National Starch;

polyamides such as the product ESTAPOR LO11 marketed by the company Rhône-Poulenc.

The alkyl radicals of the nonionic polymers have from 1 to 6 carbon atoms except where otherwise mentioned.

According to the invention, it is also possible to use fixing polymers of grafted silicone type comprising a polysiloxane portion and a portion consisting of a non-silicone organic chain, one of the two portions constituting the main chain of the polymer, the other being grafted onto the said main chain. These polymers are described, for example, in patent applications EP-A-0,412,704, EP-A-0,412,707, EP-A-0,640,105 and WO 95/00578, EP-A-0,582,152 and WO 93/23009 and U.S. Pat. Nos. 4,693,935, 4,728,571 and 4,972,037, the disclosures of which are incorporated herein by reference. These polymers are preferably anionic or nonionic.

Such polymers are, for example copolymers which can be obtained by radical polymerization starting with a monomer mixture consisting of:

(a) 50 to 90% by weight of tert-butyl acrylate;
(b) 0 to 40% by weight of acrylic acid;
(c) 5 to 40% by weight of silicone macromer of formula:

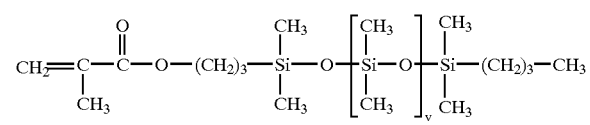

with v being a number ranging from 5 to 700; the weight percentages being calculated relative to the total weight of the monomers.

Other examples of grafted silicone polymers are, in particular, polydimethylsiloxanes (PDMS) onto which are grafted, via a connecting chain unit of thiopropylene type, mixed polymer units of the poly(meth)acrylic acid type and of the polyalkyl (meth)acrylate type and polydimethylsiloxanes (PDMS) onto which are grafted, via a connecting chain unit of thiopropylene type, polymer units of the polyisobutyl (meth)acrylate type.

According to the present invention, the fixing polymers are preferably anionic polymers.

The anionic or amphoteric fixing polymers may, if necessary, be partially or totally neutralized. The neutralizing agents are, for example, sodium hydroxide, potassium hydroxide, 2-amino-2-methyl-1-propanol, monoethanolamine, triethanolamine or triisopropanolamine, and inorganic or organic acids such as hydrochloric acid or citric acid.

According to the present invention, the term non-volatile silicone is understood to refer to any silicone having a vapour pressure, measured at 25° C. at atmospheric pressure ($10^5$ Pa), preferably of less than 0.01 mm Hg (2.6 Pa).

The non-volatile aryl silicones contain at least one radical of optionally substituted aryl type. The aryl radicals are, for example, phenyl, naphthyl, benzyl or phenethyl.

The non-volatile aryl silicones preferably have the formula (X) below:

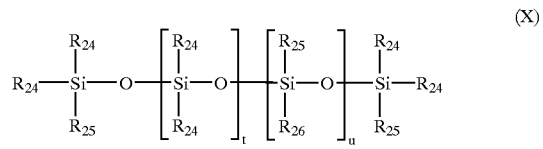

in which:

$R_{24}$, which is identical or different, denotes a $C_1$–$C_{10}$ alkyl radical, $R_{26}$, which is identical or different, denotes an aryl group, it being possible for this aryl group to comprise one or more optionally substituted aryl rings, $R_{25}$, which is identical or different, denotes $R_{26}$, $R_{24}$ or $Si(R_{24})_3$ t ranges from 0 to 1000, u ranges from 1 to 1000, the sum t+u may range from 1 to 2000.

The substituents of the aryl groups may be alkyl, alkenyl, acyl, ketone, halogens (for example Cl and Br) or amine groups. Examples of aryl groups are phenyl, a phenyl group substituted with alkyl radicals or alkenyl radicals of $C_1-C_5$ such as allylphenyl, methylphenyl, ethylphenyl, vinylphenyl and mixtures thereof.

Preferably, $R_{24}$ denotes a methyl radical. Preferably, $R_{26}$ denotes aphenyl radical.

Preferably, $R_{25}$ denotes a methyl, phenyl or trimethylsilyl radical. More preferably, the sum t+u ranges from 1 to 1000.

Among the compounds of formula (X) phenyl trimethicone, diphenyl dimethicone or phenyl dimethicone (INCI names, 5th edition, 1993) may be used, for example.

Examples of these compounds which may be mentioned are those sold by the company-Bayer under the name HUILE BAYSILONE FLUID PD5, by the company Dow Corning under the name DOW CORNING 556 FLUID, by Rhône-Poulenc under athe names MIRASIL DPDM, RHODORSIL HUILE 510 V 100, RHODORSIL HUILE 550, RHODORSIL HUILE 510V500, and RHODORSIL HUILE 710, and under the names WACKER BELSIL PDM 20, PDM 200 and PDM 1000 by the company Wacker.

According to the present invention, non-volatile aryl silicones having a refractive index of greater than 1.46, and in particular an index ranging from 1.48 to 1.7, are preferably used. The refractive index is measured using a refractometer according to well-known methods.

The fixing polymer or polymers are present, for example, in concentrations of from 0.1% to 20% by weight, and preferably in concentrations of from 1% to 10% by weight, and more particularly from 2 to 8% by weight, relative to the total weight of the composition.

The fixing polymer or polymers are present, for example, in concentrations of from 1% to 30% by weight, and: preferably in concentrations of from 2% to 15% by weight, relative to the total weight of the fluid.

The non-volatile aryl silicone or silicones may be present in concentrations of from 5% to 40% by weight, and preferably in concentrations of from 7% to 30% by weight and even more particularly from 8 to 15% by weight, relative to the total weight of the pressurized composition.

The non-volatilearyl silicone or silicones may be present in concentrations greater than or equal to 10% by weight, preferably in concentrations of from 10% to 30% by weight and even more particularly from 12 to 20% by weight, relative to the total weight of the fluid.

The cosmetically acceptable medium generally comprises solvents which are compatible with the fixing polymer and the non-volatile aryl silicone. These solvents are preferably $C_1-C_6$ alcohols which may be used alone or as a mixture.

Among these alcohols, mention may be made of ethanol, isopropanol, polyalcohols such as diethylene glycol, glycol ethers and monoalkyl ethers of glycol, of diethylene glycol, of propylene glycol or of dipropylene glycol. Ethanol is particularly preferred.

According to the invention, the non-volatile aryl silicones are preferably solubilized in the fluid.

The compositions according to the invention are preferably free of water, that is to say that they contain less than 8% by weight of water relative to the total weight of the composition, and preferably less than 5%. The compositions are thus faster to dry.

The alcohol concentration. is generally from 10 to 90% by weight and preferably from 50 to 80% by weight relative to the total weight of the pressurized composition.

The pH of the compositions according to the invention is generally from 2 to 9, and in particular from 3 to 8.5. It may be adjusted to the chosen value using basifying or acidifying agents usually used in cosmetics for this type of application.

The composition according to the invention is pressurized in the form of an aerosol; the aerosol therefore comprises the fluid (propellant-free composition) and at least one propellant which may be selected from volatile hydrocarbons such as n-butane, propane, isobutane, chloro- and/or fluorohydrocarbons and mixtures thereof. Carbon dioxide, nitrous oxide, dimethyl ether, nitrogen, compressed air and mixtures thereof may also be used as propellant.

The fluid and the propellant may be in the same compartment or in different compartments in the aerosol container.

According to the invention, the propellant concentration is generally from 5 to 90% by weight relative to the total weight of the pressurized composition, and preferably from 15 to 70% by weight.

The composition of the invention may also contain at least one additive selected from thickeners, fatty acid esters, fatty acid esters of glycerol, volatile silicones and non-aryl silicones, surfactants, fragrances, preserving agents, sunscreens, proteins, vitamins, polymers, plant, animal, mineral or synthetic oils and any other additive conventionally used in the cosmetics field.

These additives are present in the composition according to the invention in proportions which may range from 0 to 40%. by weight relative to the total weight of the composition. The precise amount of each additive depends on its nature and is readily determined by a person skilled in the art.

The compositions according to the invention may contain volatile silicones. These volatile silicones are generally present in concentrations of from 0.5% to 40% by weight, and preferably in concentrations of from 1% to 25% by weight and even more particularly from 2 to 15% by weight, relative to the total weight of the pressurized composition.

Obviously, a person skilled in the art will take care to select the optional compound or compounds to be added to the composition according to the invention such that the advantageous properties intrinsically associated with the composition in accordance with the invention are, not, or are substantially not, adversely affected by the addition envisaged.

The compositions according to the invention may be in the form of a milk, a cream or a lotion which is more or less thickened.

The compositions according to the invention may be used as rinse-out products and preferably as leave-in products in particular for retaining the shape of the hairstyle or shaping keratir substances such as the hair.

They are more particularly styling products such as fixing (lacquer) and styling compositions.

The subject of the invention is also a process for the cosmetic treatment of keratin substances such as the hair, which consists in applying thereto a composition as defined above.

The compositions according to the invention are prepared according to methods which are well known in the state of the art. In particular, the ingredients of the fluid are mixed together and then packaged in a suitable container depending on the use envisaged. The fluid is then placed in a container which is then sealed by a system including a valve, and the propellant may then be, introduced into the container.

The invention will now be illustrated more fully with the aid of the examples which follow, which should not be considered as limiting it to the embodiments described. (In the following text AM means Active Material).

EXAMPLE 1

A fixing spray composition packaged in an aerosol container and of the following composition was prepared:

| | | |
|---|---|---|
| Vinyl acetate/crotonic acid copolymer sold by the company BASF under the name LUVISET CA 66 | | 2.5 g |
| 2-Amino-2-methyl-1-propanol | qs | 100% neutralization of the polymer |
| Phenyl silicone sold under the name DC 556 by the company Dow Corning | | 5 g |
| Dimethyl ether | | 50 g |
| Ethanol | qs | 100 g |

This composition was vaporized onto dried hair; the hairstyle remained in place. The hair was very shiny and did not feel greasy.

EXAMPLE 2

A fixing spray composition packaged in an aerosol container and of the following composition was prepared:

| | | |
|---|---|---|
| Crotonic acid/vinyl acetate/vinyl neododecanoate terpolymer sold under the name RESIN 28-29-30 by the company National Starch | | 6 g |
| 2-Amino-2-methyl-1-propanol | qs | 100% neutralization of the polymer |
| Phenyl silicone sold under the name DC 556 by the company Dow Corning | | 12 g |
| Dimethyl ether | | 60 g |
| Ethanol | qs | 100 g |

The composition had the same properties as those of Example 1.

EXAMPLE 3

A fixing spray composition packaged in an aerosol container and of the following composition was prepared:

| | | |
|---|---|---|
| Acrylic acid/ethyl acrylate/n-tert-butylacrylamide terpolymer sold under the name ULTRAHOLD STRONG by the company BASF | | 4.9 g |
| 2-Amino-2-methyl-1-propanol | qs | 100% neutralization of the polymer |
| Phenyl dimethicone sold under the name BELSIL PDM 200 by the company Wacker | | 7 g |
| Dimethyl ether | | 30 g |
| Ethanol | qs | 100 g |

The composition had the same properties as those of Example 1.

EXAMPLE 4

A fixing spray composition packaged in an aerosol container and of the following composition was prepared:

| | | |
|---|---|---|
| Monoesterified methyl vinyl ether/maleic anhydride copolymer sold by the company ISP under the name GANTREZ ES 425 | | 6 g |
| 2-Amino-2-methyl-1-propanol | qs | 20% neutralization of the polymer |
| Diphenyl dimethicone sold under the name MIRASIL DPDM by the company Rhône-Poulenc | | 15 g |
| Dimethyl ether | | 50 g |
| Ethanol | qs | 100 g |

The composition had the same properties as those of Example 1.

EXAMPLE 5

A fixing spray composition packaged in an aerosol container and of the following composition was prepared:

| | | |
|---|---|---|
| Acrylic acid/ethyl acrylate/n-tert-butylacrylamide terpolymer sold under the name ULTRAHOLD STRONG by the company BASF | | 7 g |
| 2-Amino-2-methyl-1-propanol | qs | 100% neutralization of the polymer |
| Phenyl silicone sold under the name DC 556 by the company Dow Corning | | 15 g |
| Dimethyl ether | | 40 g |
| Ethanol | qs | 100 g |

The composition had the same properties as those of Example 1.

What is claimed is:

1. A cosmetic aerosol-pressurized composition comprising:
   (a) a fluid comprising, in a cosmetically acceptable medium, at least one fixing polymer and at least one non-volatile aryl silicone and
   (b) at least one propellant present in an amount ranging from 15% to 90% by weight relative to the total weight of the composition,
   wherein said at least one non-volatile aryl silicone is present in an amount greater than or equal to 5% by weight relative to the total weight of the composition and
   wherein said cosmetic aerosol-pressurized composition is in the form of an aerosol spray composition.

2. A composition according to claim 1, wherein said at least one fixing polymer is present in an amount ranging from 0.1% to 20% by weight relative to the total weight of the composition.

3. A composition according to claim 2, wherein said at least one fixing polymer is present in an amount ranging from 1% to 10% by weight relative to the total weight of the composition.

4. A composition according to claim 3, wherein said at least one fixing polymer is present in an amount ranging from 2% to 8% by weight relative to the total weight of the composition.

5. A composition according to claim 1, wherein said at least one non-volatile aryl silicone is present in an amount ranging from 5% to 40% by weight relative to the total weight of the composition.

6. A composition according to claim 5, wherein said at least one non-volatile aryl silicone is present in an amount ranging from 7% to 30% by weight relative to the total weight of the composition.

7. A composition according to claim 1, wherein said at least one non-volatile aryl silicone is present in an amount ranging from 10% to 40% by weight relative to the total weight of the fluid.

8. A composition according to claim 7, wherein said at least one non-volatile aryl silicone is present in an amount ranging from 15% to 30% by weight relative to the total weight of the fluid.

9. A composition according to claim 1, wherein said at least one fixing polymer is selected from anionic, cationic, amphoteric and nonionic polymers.

10. A composition according to claim 9, wherein said anionic fixing polymer is selected from:
polymers containing carboxylic units derived from unsaturated mono- or dicarboxylic acid monomers of formula

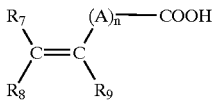

(II)

in which n is an integer from 0 to 10,
A denotes a methylene group, optionally linked to the carbon atom of the unsaturated group or to the neighbouring methylene group when n is greater than 1 via a hetero atom,
$R_7$ denotes a hydrogen atom, a phenyl group or a benzyl group,
$R_8$ denotes a hydrogen atom or a $C_1$–$C_6$ lower alkyl or carboxyl group, and
$R_9$ denotes a hydrogen atom, a $C_1$–$C_6$ lower alkyl group, a —$CH_2$—COOH group, a phenyl group or a benzyl group; and
polymers comprising units derived from sulphonic acid.

11. A composition according to claim 10, wherein said hetero atom is oxygen or sulphur.

12. A composition according to claim 10, wherein said units derived from sulphonic acid are selected from vinylsulphonic, styrenesulphonic and acrylamidoalkylsulphoic units.

13. A composition according to claim 10, wherein said anionic fixing polymer is selected from:
(A) homo- or copolymers of acrylic acid or methacrylic acid and salts thereof, copolymers of acrylic acid and of acrylamide and salts thereof, and salts of polyhydroxycarboxylic acids;
(B) copolymers of acrylic acid or methacrylic acid with a monoethylenic monomer, optionally grafted onto a polyalkylene glycol and optionally crosslinked;
copolymers of acrylic acid or methacrylic acid with a monoethylenic monomer, optionally grafted onto a polyalkylene glycol and optionally crosslinked, containing an N-alkylated or hydroxyalkylated acrylamide unit or an N-alkylated and hydroxyalkylated acrylamide unit in their chain, copolymers of acrylic acid and of $C_1$–$C_4$ alkyl methacrylate;
(C) copolymers derived from crotonic acid, wherein said copolymers are optionally grafted and crosslinked;
(D) copolymers derived from $C_4$–$C_8$ monounsaturated carboxylic acids or anhydrides selected from:
copolymers comprising (i) one or more maleic, fumaric or itaconic acids or anhydrides and (ii) at least one monomer selected from vinyl esters, vinyl ethers, vinyl halides, phenylvinyl derivatives, acrylic acid, and acrylic acid esters, wherein the anhydride functions of said copolymers are optionally being monoesterfied or monoamidated;
copolymers comprising (i) one or more maleic, citraconic or itaconic anhydrides and (ii) one or more monomers selected from allylic or methallylic esters optionally containing one or more acrylamide, methacrylamide or α-olefin group, acrylic or methacrylic esters, acrylic or methacrylic acids or vinylpyrrolidone in their chain, wherein the anhydride functions of said copolymers are optionally monoesterfied or monoamidated; and
(E) polyacrylamides containing carboxylate groups.

14. A composition according to claim 13, wherein said monoethylenic monomer is selected from ethylene, styrene, vinyl esters, esters of acrylic acid, and esters of methacrylic acid.

15. A composition according to claim 13, wherein said polyalkylene gylcol is polyethylene glycol.

16. A composition according to claim 13, wherein said copolymers derived from crotonic acid contain vinyl acetate or propionate units and optionally other monomers selected from allylic or methallylic esters, vinyl ether or vinyl ester of a linear or branched saturated carboxylic acid with a long hydrocarbon chain.

17. A composition according to claim 16, wherein said long hydrocarbon chain contains at least 5 carbon atoms.

18. A composition according to claim 13, wherein said anionic fixing polymer is selected from:
acrylic acid copolymers;
copolymers derived from crotonic acid;
polymers derived from maelic, fumaric or itaconic acids or anhydrides with vinyl esters, vinyl ethers, vinyl halides, phenylvinyl derivatives, and acrylic acid and esters thereof;
copolymers of methacrylic acid and of methyl methacrylate;
the copolymer of methacrylic acid and of ethyl acrylate;
vinyl acetate/crotonic acid copolymer; and
vinyl acetate/crotonic acid copolymer grafted with polyethylene glycol.

19. A composition according to claim 18, wherein said anionic fixing polymer is selected from acrylic acid/ethyl acrylate/N-tert-butylacrylamide terpolymers.

20. A composition according to claim 18, wherein said anionic fixing polymer is selected from vinyl acetate/vinyl tert-butylbenzoate/crotonic acid terpolymers and crotonic acid/vinyl acetate/vinyl neododecanoate terpolymers.

21. A composition according to claim 18, wherein said anionic fixing polymer is selected from monoesterified methyl vinyl etherimaleic anhydride terpolymers.

22. A composition according to claim 9, wherein said amphoteric fixing polymer is selected from polymers containing units derived from:
a) at least one monomer selected from acrylamides or methacrylamides substituted on the nitrogen with an alkyl radical,
b) at least one acidic comonomer containing one or more reactive carboxylic group, and
c) at least one basic comonomer.

23. A composition according to claim 22, wherein said at least one basic comonomer is selected from esters containing primary, secondary, tertiary or quaternary amine substituents of acrylic acid or methacrylic acids, and the product of quaternization of dimethylaminoethyl methacrylate with dimethyl or diethyl sulphate.

24. A composition according to claim 22, wherein said amphoteric fixing polymer is selected from octylacrylamide/acrylates/butylaminoetyl methacrylate copolymers and copolymers of methyl methacrylate/methyl dimethylcarboxymethylammonioethylmethacrylate.

25. A composition according to claim 9, wherein said nonionic fixing polymer is selected from:
polyalkyloxazolines;
vinyl acetate homopolymers;
copolymers of vinyl acetate and of acrylic ester;
copolymers of vinyl acetate and of ethylene;
copolymers of vinyl acetate and of maleic ester;
vinyl chloride homopolymers;
polyethylene waxes;
polyethylene/polytetrafluoroethylene waxes;
copolymers of polyethylene and of maleic anhydride;
alkyl acrylate homopolymers and alkyl methacrylate homopolymers;
copolymers of acrylic esters;
copolymers of acrylonitrile and a nonionic monomer;
styrene homopolymers;
copolymers of styrene and alkyl (meth)acrylate;
copolymers of styrene, alkyl methacrylate and alkyl acrylate;
copolymers of styrene and of butadiene;
copolymers of styrene, of butadiene and of vinyl pyridine; and
copolymers of alkyl acrylate and of urethane.

26. A composition according to claim 25, wherein said nonionic fixing polymeris selected from copolymers of alkyl acrylates and alkyl methacrylates.

27. A composition according to claim 25 wherein said nonionic monomer is selected from butadiene and alkyl (meth)acrylates.

28. A composition according to claim 9 wherein said cationic fixing polymer is selected from:
copolymers of acrylamide and of dimethylaminoethyl methacrylate quaternized with dimethyl sulphate;
copolymers of acrylamide and of methacryloyloxyethyltrimethylammonium chloride;
copolymers of acrylamide and of methacryloyloxyethyltrimethylammonium methosulphate;
quaternized or non-quaternized vinylpyrrolidone/dialkylaminoalkyl acrylate copolymers;
dimethylaminoethyl methacrylate/vinylcaprolactam/vinylpyrrolidone terpolymers; and
quaternized vinylpyrrolidone/dimethylaminopropyl methacrylamide copolymers.

29. A composition according to claim 1, wherein said non-volatile aryl silicones are selected from silicones of formula (X):

$$R_{24}-\underset{\underset{R_{25}}{|}}{\overset{\overset{R_{24}}{|}}{Si}}-O-\left[\underset{\underset{R_{24}}{|}}{\overset{\overset{R_{24}}{|}}{Si}}-O\right]_t\left[\underset{\underset{R_{26}}{|}}{\overset{\overset{R_{25}}{|}}{Si}}-O\right]_u\underset{\underset{R_{25}}{|}}{\overset{\overset{R_{24}}{|}}{Si}}-R_{24}$$

(X)

in which:
$R_{24}$, which is identical or different, denotes a $C_1$–$C_{10}$ alkyl radical, $R_{26}$, which is identical or different, denotes an aryl group, which may comprise one or more optionally substituted aryl rings, $R_{25}$, which is identical or different, denotes $R_{26}$, $R_{24}$ or $Si(R_{24})_3$ t ranges from 0 to 1000, u ranges from 1 to 1000, the sum t+u ranges from 1 to 2000.

30. A composition according to claim 29, wherein said aryl group is selected from phenyl groups substituted with alkyl radicals or alkenyl radicals of $C_1$–$C_5$ and mixtures thereof.

31. A composition according to claim 30, wherein said at least one non-volatile aryl silicone is selected from phenyl trimethicone, diphenyl dimethicone and phenyl dimethicone.

32. A composition according to claim 1, wherein said cosmetically acceptable medium comprises $C_1$–$C_6$ alcohols.

33. A composition according to claim 1, further comprising at least one volatile silicone.

34. A composition according to claim 33, wherein said at least one volatile silicone is present in an amount ranging from 1% to 40% by weight relative to the total weight of the composition.

35. A composition according to claim 1, wherein said at least one propellant is selected from volatile hydrocarbons.

36. A composition according to claim 35, wherein said volatile hydrocarbons are selected from n-butane, propane, isobutane, chlorohydrocarbons, fluorohydrocarbons, carbon dioxide, nitrous oxide, dimethyl ether, nitrogen, compressed air and mixtures thereof.

37. A composition according to claim 1, wherein said at least one propellant is present in an amount ranging from 30% to 90% by weight relative to the total weight of the composition.

38. A composition according to claim 1, wherein said at least one propellant is present in an amount ranging from 15 to 70% by weight relative to the total weight of the composition.

39. A process for the cosmetic treatment of a keratin substance comprising applying to said keratin substance an effective amount of a composition according to claim 1.

40. A process for styling or fixing hair comprising applying to said hair an effective amount of a composition according to claim 1.

41. A cosmetic aerosol-pressurized composition comprising:
(a) a fluid comprising, in a cosmetically acceptable medium, at least one fixing polymer and at least one non-volatile aryl silicone and
(b) at least one propellant,
wherein said at least one non-volatile aryl silicone is present in an amount greater than or equal to 5% by weight relative to the total weight of the composition and
wherein said cosmetic aerosol-pressurized composition is in the form of an aerosol spray composition.

42. A process for treating a keratin substance comprising applying to said keratin substance said cosmetic aerosol-pressurized composition according to claim 41.

43. A process for styling or fixing hair comprising applying to said hair cosmetic aerosol-pressurized composition according to claim 41.

* * * * *

UNITED STATES PATENT AND TRADEMARK OFFICE
CERTIFICATE OF CORRECTION

PATENT NO.     : 6,503,479 B1  Page 1 of 1
DATED          : January 7, 2003
INVENTOR(S)    : Claire-Marie Lesaulnier et al.

It is certified that error appears in the above-identified patent and that said Letters Patent is hereby corrected as shown below:

<u>Title page,</u>
Item [75], the Inventor surname "LesAulnier" should read -- Lesaulnier --.

<u>Column 17,</u>
Lines 46-47, "acrylamidoalkylsulphoic" should read -- acrylamidoalkylsulphonic --.

<u>Column 18,</u>
Lines 7 and 15, "monoesterfied" should read -- monoesterified --.
Line 23, "gylcol" should read -- glycol --.
Line 36, "maelic" should read -- maleic --.
Line 56, "etherimaleic" should read -- ether/maleic --.
Line 64, "group" should read -- groups --.

<u>Column 19,</u>
Line 7, "butylaminoetyl" should read -- butylaminoethyl --.
Line 36, "polymeris" should read -- polymer is --.

<u>Column 20,</u>
Lines 34-35, "from 30%" should read -- from greater than 30% --.

Signed and Sealed this

Tenth Day of June, 2003

JAMES E. ROGAN
*Director of the United States Patent and Trademark Office*